United States Patent [19]

Schmidt et al.

[11] 4,395,422

[45] Jul. 26, 1983

[54] SPRAY DRIED VITAMIN E POWDER

[75] Inventors: Douglass N. Schmidt, Grosse Ile, Mich.; Frank Fischetti, Jr., Flushing, N.Y.

[73] Assignee: BASF Wyandotte Corporation, Wyandotte, Mich.

[21] Appl. No.: 251,076

[22] Filed: Apr. 6, 1981

[51] Int. Cl.³ ........................................... A01N 43/16
[52] U.S. Cl. ................................................... 424/284
[58] Field of Search ........................................ 424/284

[56] References Cited

U.S. PATENT DOCUMENTS 3,914,430 10/1975 Cannalonga et al. ............... 424/284
3,962,384  6/1976 Cannalonga et al. ............... 424/284
4,262,017  4/1981 Kuipers et al. ..................... 424/284

Primary Examiner—Elbert L. Roberts
Attorney, Agent, or Firm—Andrew E. Pierce

[57] ABSTRACT

Spray dried vitamin E powders comprising 50 to 56 percent by weight vitamin E, 1 to 25 percent by weight hydrolyzed gelatin and 20 to 30 percent by weight caseinate. The resulting powders can be directly compressed into tablets of improved hardness and friability.

8 Claims, No Drawings

SPRAY DRIED VITAMIN E POWDER

BACKGROUND OF THE INVENTION

1. Field of the Invention

The invention relates to a dry, free flowing vitamin E powder produced by spray drying a vitamin E emulsion. More particularly the invention relates to a spray dried vitamin E powder, suitable for direct compression, containing vitamin E acetate, caseinate, hydrolyzed gelatin, and silicon dioxide.

2. Description of the Prior Art

The preparation of vitamin E powders containing 40 to 60 percent by weight hydrolyzed gelatin has been disclosed in U.S. Pat. No. 3,608,083, Bunnell et al., Sept. 21, 1971. U.S. Ser. No. 38,258, Kuipers et al. filed May 11, 1979 relates to a process for preparing vitamin E powder from an emulsion containing sodium or potassium caseinate dissolved in a residual liquor from the production of lactose. U.S. Pat. No. 3,962,384 relates to a process of spray drying vitamin powders with silicon dioxide.

Some of the problems associated with prior art powders such as those described in the above-mentioned references include particle agglomeration, poor color and/or odor, and reduced flowability of the powders into the tablet press thereby causing sticking and poor tabletting. Some of the problems associated with the tablets made from prior art powders include capping, chipping and picking as well as poor color, increased friability and decreased hardness.

The present invention is directed toward novel vitamin E powders of improved flow which provide directly compressible tablets of improved hardness and friability.

SUMMARY OF THE INVENTION

The invention relates to a spray dried vitamin E powder suitable for direct compression tablets comprising 20 percent by weight to 60 percent by weight, preferably 50 percent by weight to 56 percent by weight, vitamin E, 0 percent by weight to 2 percent by weight fatty acid monoglyceride, preferably 1 percent by weight to 1.5 percent by weight, 1 percent by weight to 25 percent by weight, preferably 10 percent by weight to 22 percent by weight hydrolyzed gelatin, about 20 percent by weight to about 30 percent by weight, preferably 20 percent by weight to 27 percent by weight, caseinate, and 0.5 percent by weight to 2.0 percent by weight, preferably 1.0 percent by weight to 2.0 percent by weight, silicon dioxide, all based on the weight of the powder, and 0 percent by weight to 22 percent by weight, preferably 9 percent by weight to 15 percent by weight, lactose.

In another aspect of the invention, an emulsion is prepared of 22 to 28 percent by weight vitamin E. 0 to 1 percent by weight monoglyceride, 0 to 11 percent by weight lactose, 0.4 to 13 percent by weight hydrolyzed gelatin, 8 to 14 percent by weight sodium caseinate and at least 45 percent by weight, preferably 45 to 60 percent by weight water, all based on the weight of the emulsion; the emulsion having a viscosity of between 200 cps and 1000 cps., preferably 400 cps. and 600 cps. The emulsion is then spray dried, to produce a vitamin E powder, in the presence of 0.5 percent by weight to 2.0 percent by weight silicon dioxide, based on the weight of powder.

DESCRIPTION OF THE PREFERRED EMBODIMENTS

The vitamin E used to provide vitamin E activity in the powder of this invention is a tocopherol or an ester thereof. α-Tocopherol has the greatest biological activity while the isomers beta, gamma and delta tocopherol have a lesser activity. The tocopherols and their esters such as tocopheryl acetate and tocopheryl succinate are normally water insoluble and oily, waxy or low melting. Therefore in making water dispersible powders, an emulsion is normally prepared and then spray dried. D-α-tocopherol and d-α-tocopheryl acetate are of use in the invention. Preferably used is vitamin E acetate. More preferably used is dl-α-tocopheryl acetate.

The powder of this invention contains between about 20 and about 30, preferably 20 and 27 percent by weight of a caseinate. Examples of caseinate of use in the invention are casein, neutralized by a suitable base such as sodium hydroxide or potassium hydroxide, and preferably sodium caseinate and potassium caseinate. Casein, derived from milk protein, is a colloidal aggregate composed of several proteins together with phosphorus and calcium. More preferably used is sodium caseinate which is spray dried, totally reacted, flavor, color, reduced milk protein manufactured from selected, premium quality edible casein. The sodium caseinate level should be greater than about 20 percent by weight based on the dry powder. As comparison Examples E and F show, 14 percent by weight or 15 percent by weight caseinate does not provide direct compression tablettable powders.

Suitable hydrolyzed gelatin for use in the powder of this invention has a molecular weight of about 9000 to about 11,000 and 0 bloom. Preferably used is 1 percent by weight to 25 percent by weight. More preferably used is 10 percent by weight to 22 percent by weight. The weight ratio of caseinate to hydrolyzed gelatin should be greater than 1:1.

A fatty acid monoglyceride, from 0 percent by weight to 1.5 percent by weight, preferably 1.0 percent by weight to 1.5 percent by weight is used as a secondary emulsifier in preparing the powders of the invention. The monoglyceride is a glycerol ester of a fatty acid wherein only one acid group is attached to the glycerol. Preferably used is between 1.0 percent by weight to 1.5 percent by weight of a monoglyceride which is a mixture of glycerol monostearate and glycerol monopalmitate, about 90 percent by weight monoglyceride, derived from hydrogenated tallow or lard and includes about 10 percent by weight diglycerides. The monoglyceride promotes the formation of small emulsion droplets, increases the drying rate and assists in the disintegration (dissolution) of the tablets. Water, preferably deionized water, is used in the emulsion.

The emulsions of the invention are spray dried in the presence of silicon dioxide. Preferably used is silicon dioxide of colloidal particle size, i.e. from 1 nanometer (1 millimicron) to 1 micron. More preferably used is a silicon dioxide, containing less than 0.2 percent by weight of other materials, of an average primary particle size of about 12 nanometers, a surface area of about 200 square meters per gram, a tap density of about 50 grams per liter, a moisture content of 1.5 percent by weight maximum (2 hours at 105° C.), on ignition loss of 1 percent by weight maximum (2 hours at 1000° C.) and a pH of 3.6–4.3 (4 percent by weight aqueous dispersion).

A tabletting excipient, from 0 to 11 percent by weight, preferably 4.5 to 7.5 percent by weight, may be added to the emulsion to aid in preparing the powders of the invention. Examples of these excipients are disaccharide sugars, as for example, lactose, sucrose, maltose and cellobiose.

Other optional additives are preservatives as mentioned in U.S. Pat. No. 3,608,083, column 2, lines 27-42.

In preparing the emulsions in accordance with this invention, the vitamin E, water, caseinate, hydrolyzed gelatin, optional monoglyceride, optional disaccharide and other optional additives are fed to a mixing vessel. After the materials are mixed to a slurry in the mixing vessel, the slurry is fed through a homogenizer to a spray dryer. The viscosity of the emulsion varies with the water content of the emulsion and the caseinate level. The viscosity of the emulsion is largely independent of the hydrolyzed gelatin level.

Any suitable mixing vessel may be used. Any suitable homogenizer may be used which makes emulsion droplets of less than about 2 microns and a viscosity up to 1000 cps, preferably between 200 and 1000 cps. Any suitable spray dryer may be used, preferably a vertical spray dryer equipped with a means of making droplets, such as a rotary atomizer operated between 14,000 and 25,000 rpm, preferably 20,000 to 23,000 rpm. The inlet temperature is maintained at 390° to 420° F. and the outlet temperature is a function of the inlet temperature and flow rate usually between 190° and 195° F. From 0.5 to 2.5 percent by weight, based on the weight of dry powder, of silicon dioxide is added to the dryer chamber, preferably at a point of negative pressure. The emulsion is spray dried to form a non-agglomerated powder.

In the preparation of a powder suitable for direct compression into pharmaceutical grade vitamin tablets, it is important to minimize the extrusion of oil from the powder. Unsuitable, oily (high surface oil) powders may flow poorly in the tableting press or stick in the die of the tablet press. Tablets made from unsuitable powders may have incomplete shapes, i.e. due to picking in the center of the tablet, capping of the tablets, or chipping on the edge of the tablet.

The powder particles of the invention are non-agglomerated and free flowing when compared with powders made by a prior art process of spray drying agglomeration. Methods of determining angle of repose, used in determining the free flowing property of powders, are mentioned in "Some Aspects of the Property of Angle of Repose of Powder," David Train, *J. Pharm. Pharmac.*, Vol. 10, 1958, pages 127T to 135T.

The tablets are made by conventional methods. Useful tabletting aids are disclosed in *Pharmaceutical Technology*, July 1980, pages 27 to 35 and 62.

Examples of uses of the vitamin E powders of the invention are direct compression vitamin E tablets, a component in multi-vitamin tablets, as well as a component in the preparation of animal feed supplements.

Following are definitions of angle of repose, tablet hardness and tablet friability used in the tablet tests.

TABLET HARDNESS

A measure of the strength of tablets (average of ten or more tablets) and their ability to retain their physical integrity, expressed in terms of Strong Cobb Units (S.C.U.), as determined by conventional procedure using a Strong Cobb Hardness tester of the Strong-Cobb-Arner Company, Cleveland, Ohio, or an equivalent type hardness tester and the average of these readings is reported herein as "hardness."

TABLET FRIABILITY

A measure of the tendency of tablets (average of 10 or more tablets) to cap, chip, or wear and usually expressed in terms of percent weight loss, as determined by a test described in the Journal of the American Pharmaceutical Association, Scientific Edition, Vol. 45, pages 114-116 (1956). This is conducted by sampling ten or more tablets from each batch by first de-dusting the tablets and weighing the same. The tablets are then subjected to the friability test in a "Roche Friabilator" at 20 revolutions per minute for a time period of ten minutes. The tablets are allowed to roll and fall for a given time and thereafter de-dusted and weighed again. The loss of weight is reported as percentage loss from the original weight. It is well known that an active ingredient-containing tablet displaying a weight loss of less than about 1 percent (moderate wearing) generally is considered to have acceptable friability. Such a tablet characteristic is herein defined as "substantially non-friable."

ANGLE OF REPOSE

In order to show the free flowing property of the powders of the invention, an angle of repose test was conducted. Methods of determining angle of repose are mentioned in "Some Aspects of the Property of Angle of Repose of Powder," David Train, supra. In order to determine the angle of repose of powders of the invention, and comparison powders, 100 grams of test powder was placed in a glass pyrex 60° funnel of 98 millimeter diameter and a stem diameter of 15 millimeters. The funnel was positioned on a ring stand with the stem tip 4 inches above the table. The flow rate was measured in seconds from the beginning to end of flow and the angle of repose was measured as an angle from the horizontal table surface.

The following Examples illustrate the invention. In the Examples, unless otherwise stated, all parts are by weight.

EXAMPLE I AND COMPARISON EXAMPLE A

A slurry was made in a stainless steel jacketed tank equipped with an anchor agitator. This slurry was emulsified by passing the slurry through a homogenizer until the droplet size of the emulsion was between 1 micron and 2 microns (viscosity—400-600 cps.).

The emulsion contained:

| Component | Parts |
|---|---|
| deionized water | 1565.4 |
| lactose | 200.8 |
| sodium caseinate[1] | 280.0 |
| hydrolyzed gelatin | 138.8 |
| distilled monoglyceride | 15.7 |
| vitamin E acetate | 752.9 |

[1]The lactose and sodium caseinate were mixed in a ribbon blender before adding to the deionized water at a temperature between 60° C. and 65° C.

The emulsion, at a temperature between 60° C. and 65° C., was sprayed into a 9 foot diameter vertical spray dryer through a rotary atomizer at 20,000 to 23,000 revolutions per minute. About 2 percent by weight, based on the weight of the powder, of silicon dioxide was added as an absorbent into the drying chamber at a point of negative pressure.

1354 parts of a spray dried powder were made which contained:

| Component | Percent by Weight Based on the Weight of Dry Powder |
|---|---|
| lactose | 14.32 |
| sodium caseinate | 19.98 |
| hydrolyzed gelatin | 9.90 |
| distilled monoglyceride | 1.12 |
| Vitamin E acetate | 53.69 |
| silicon dioxide | 1.0 |

The moisture content of the resultant dry powder was 1.5 percent by weight. The particle size of the powder was between about 60 and about 100 mesh. The actual vitamin E activity as determined by GLC assay was 51.8 percent by weight. Ash content was 1.49 percent by weight. Bulk density was 46.53 grams per 100 milliliters.

Powders had the following properties:

| | |
|---|---|
| Angle of repose in degrees | 28–34 |
| Flow rate in seconds/100 grams | 5.25–5.36 |

Chewable Vitamin E tablets containing about 53 percent vitamin E powder or 200 international units were prepared using a standard tablet formulation consisting of a directly compressible sugar, glidants, a lubricant, flavoring, color and additives in a room with temperature of 68° F. and relative humidity of 47 percent. Tablet thickness was adjusted to achieve optimized hardness and friability Tablets were made on a single rotary tablet press at 30 revolutions per minute to give tablets of the following properties:

| | |
|---|---|
| thickness | 6.32–6.43 millimeters |
| disintegration time | 31–39 minutes |
| friability | moderate wearing, no chipping |
| hardness | 9.8 (SCU) |

COMPARISON EXAMPLE A

Comparison tablets were similarly made from a commercially available prior art spray dried vitamin E powder. The powder contained between 40 and 60 percent by weight hydrolyzed gelatin, vitamin E acetate, and other conventional materials.

Chewable Vitamin E tablets were prepared using a standard tablet formulation as above in a room with a temperature of 70° F. and relative humidity of 65 percent. The same tabletting conditions as above were conducted to give tablets of the following properties:

| | |
|---|---|
| thickness | 6.61–6.73 millimeters |
| disintegration time | 22–27 minutes |
| hardness | 8.45 SCU |
| friability | moderate chipping |

The tablets of this invention exhibited increased hardness and an improved friability, i.e. wearing.

EXAMPLES 2–8 AND COMPARISON EXAMPLES B–D

The results of tests run on powders of the invention and comparison powders are shown in Tables 1, 2 and 3 below. Lactose is a tabletting excipient. The closer to the flow rate of lactose, angle of repose—30°, flow rate 3.49 seconds per 100 grams, the better the flow properties of the powders of the invention. The powders of Examples 2–4 of the invention showed an improved flow when compared to Example A and Example B. The results of the tabletting test show that some of the powders of the invention have improved flow when compared to the prior art and that the tablets made from powders of the invention have improved hardness and friability when compared with tablets of the prior art.

Comparison Example B is a powder containing 33 to 35 percent by weight gelatin, 2.0 percent silica absorbent, 10 percent by weight lactose, and remainder vitamin E acetate.

Comparison Example C is a vitamin E powder containing 56.0 percent by weight vitamin E acetate, 34.5 percent by weight lactose, 7.3 percent by weight sodium caseinate, 1.12 percent by weight distilled monoglyceride, and 1.0 percent by weight silicon dioxide.

Comparison Example D is a vitamin E powder containing 54.3 percent by weight vitamin E acetate, 19.42 percent by weight lactose, 25.1 percent by weight sodium caseinate, 1.13 percent by weight distilled monoglyceride, and 0.75 percent by weight silicon dioxide.

TABLE 1

| | Example | | | | | |
|---|---|---|---|---|---|---|
| | 2 | | 3 | | 4 | |
| | [parts] Emulsion | [%/wt] Powder | [parts] Emulsion | [%/wt] Powder | [parts] Emulsion | [%/wt] Powder |
| Sodium Caseinate | 28.98 | 20.55 | 28.20 | 20.0 | 36.6 | 27.1 |
| Hydrolyzed Gelatin | 14.64 | 10.38 | 21.18 | 15.0 | 1.35 | 1.0 |
| Lactose | 20.91 | 14.82 | 13.62 | 9.67 | 22.38 | 16.58 |
| Monoglyceride, distilled | 0 | 0 | 1.59 | 1.13 | 1.53 | 1.13 |
| Vitamin E Acetate | 76.47 | 54.23 | 76.41 | 54.2 | 73.14 | 54.2 |
| Deionized Water | 159.0 | | 159.0 | | 183.0 | |
| Silicon Dioxide in parts | | 2 | | 2.5 | | 3 |
| Product Yield in parts | | 84 | | 130 | | 109 |
| Powders | | | | | | |
| Angle of Repose [degrees] | | 30 | | 28–30 | | 30 |
| Flow Rate [seconds/100 grams] | | 4.29–5.30 | | 4.22–4.31 | | 5.05–5.16 |
| Tablets | | | | | | |
| Disintegration Time [minutes] | | | | 48–54 | | 46–52 |
| Hardness SCU | | | | 8.7 | | 9.1 |

TABLE 1-continued

|  | Example | | | | | |
|---|---|---|---|---|---|---|
|  | 2 | | 3 | | 4 | |
|  | [parts] Emulsion | [%/wt] Powder | [parts] Emulsion | [%/wt] Powder | [parts] Emulsion | [%/wt] Powder |
| Friability** |  |  |  | MW |  | SMW |

**SW = slight wearing
SMW = slight to moderate wearing
MW = moderate wearing
MC = moderate chipping

TABLE 2

|  | Example | | | | | | | |
|---|---|---|---|---|---|---|---|---|
|  | 5 | | 6 | | 7 | | 8 | |
|  | [parts] Emulsion | [%/wt] Powder | [parts] Emulsion | [%/wt] Powder | [parts] Emulsion | [%/wt] Powder | [parts] Emulsion | [%/wt] Powder |
| Sodium Caseinate | 25.2 | 20.0 | 27.0 | 20.0 | 31.95 | 23.67 | 28.11 | 20.53 |
| Hydrolyzed Gelatin | 12.6* | 10.0* | 27.0 | 20.0 | 28.35 | 21.0 | 14.22 | 10.39 |
| Lactose | 18.48 | 14.67 | 6.3 | 4.67 | 0 | 0 | 20.31 | 14.83 |
| Monoglyceride, distilled | 1.14 | 1.12 | 1.53 | 1.13 | 1.53 | 1.13 | 0 | 0 |
| Vitamin E Acetate | 68.31 | 54.2 | 73.17 | 54.2 | 73.17 | 54.2 | 74.25 | 54.20 |
| Deionized Water | 174.0 |  | 183.0 |  | 183.0 |  | 172.0 |  |
| Silicon Dioxide in parts |  | 3 |  | 3 |  | 2.5 |  | 4.5 |
| Product Yield in parts |  | 109 |  | 109 |  | 111 |  | 123 |
| Powders |  |  |  |  |  |  |  |  |
| Angle of Repose in degrees |  | 32 |  | 30-32 |  | 32 |  | 31-34 |
| Flow Rate in seconds/100 grams |  | 6.73-8.59 |  | 5.38-5.52 |  | 7.84-8.95 |  | 7.10-9.40 |
| Tablets |  |  |  |  |  |  |  |  |
| Disintegration Time [minutes] |  | Sticking |  | 38-46 |  | 48-53 |  | 56-67 |
| Hardness SCU |  | no |  | 9.0 |  | 11.7 |  | 9.4 |
| Friability** |  | tablets |  | SW |  | SW |  | SMW |

*Molecular Weight = 2000
**SW = slight wearing
SMW = slight to moderate wearing
MW = moderate wearing
MC = moderate chipping

TABLE 3

|  | Example | | |
|---|---|---|---|
|  | B | C | D |
| Powders |  |  |  |
| Angle of Repose - degrees | 42 | 50 | 30 |
| Flow Rate - seconds/100 grams | No flow | No flow | 5.18 |
| Tablets |  |  |  |
| Disintegration time - minutes | 33-37 | Sticking | 31-43 |
| Hardness S.C.U. | 10.85 | no | 8.6 |
| Friability** | MW | tablets | HC |

**MW = moderate wearing
HC = heavy chipping

COMPARISON EXAMPLES E AND F

Comparison Examples E and F show that powders with less than 20 percent of caseinate or with a predominance of hydrolyzed gelatin cannot be directly compressed into tablets.

|  | E | F |
|---|---|---|
| Sodium Caseinate | 14.1 | 15.0 |
| Hydrolyzed gelatin | 16.0 | 20.0 |
| Lactose | 14.5 | 9.6 |
| Monoglyceride distilled | 1.2 | 1.2 |
| Vitamin E acetate | 54.2 | 54.2 |
| Silicon dioxide | 0.75 | 0.75 |

When the powders of Examples E and F were fed to the tabletting press, the powder stuck in the tabletting chamber, preventing tabletting.

The embodiments of the invention in which an exclusive property or privilege is claimed are defined as follows:

1. A vitamin E powder suitable for the preparation of direct compression vitamin tablets comprising 20 to 60 percent by weight Vitamin E, 0.5 to 2.0 percent by weight silicon dioxide having a particle size of 1 millimicron to 1 micron, 1 to 25 percent by weight hydrolyzed gelatin, and about 20 to 30 percent by weight caseinate, with the proviso that the weight ratio of caseinate to gelatin be greater than 1:1 all weight based on the total weight of powder.

2. A vitamin E powder suitable for the preparation of direct compression vitamin tablets consisting essentially of 50 percent by weight to 56 percent by weight of vitamin E, 0.5 percent by weight to 2.0 percent by weight of silicon dioxide having a particle size of 1 millimicron to 1 micron, 1 percent by weight to 25 percent by weight of a hydrolyzed gelatin, about 20 percent by weight to about 30 percent by weight of a caseinate and the remainder to 100 percent by weight of a monoglyceride and/or a tabletting excipient, with the proviso that the weight ratio of caseinate to gelatin be greater than 1:1, all weights based on the total weight of powder.

3. The powder of claim 2 wherein the vitamin E is vitamin E acetate.

4. The powder of claim 2 wherein the tabletting excipient is lactose.

5. The powder of claim 2 containing from 1.0 to 1.5 percent by weight monoglyceride.

6. A vitamin E acetate powder suitable for the preparation of direct compression vitamin tablets comprising 50 percent by weight to 56 percent by weight vitamin E acetate, 1.0 percent by weight to 2.0 percent by weight silicon dioxide having a particle size of 1 millimicron to 1 micron, 1.0 percent by weight to 1.5 percent by weight distilled monoglyceride, 0 percent by weight to 22 percent by weight lactose, 10 percent by weight to 22 percent by weight hydrolyzed gelatin, and 20 percent by weight to 27 percent by weight caseinate, with the proviso that the weight ratio of caseinate to gelatin be greater than 1:1, all weights based on the total weight of powder.

7. The powder of claim 6 containing 9 to 15 percent by weight lactose.

8. A process for the preparation of spray dried vitamin E powder comprising:
   A. emulsifying to a particle size of less than about 2 microns and a viscosity up to 1000 cps, 45 to 60 percent by weight deionized water, 22 to 28 percent by weight vitamin E acetate, 8 to 14 percent by weight caseinate, 0.4 to 13 percent by weight hydrolyzed gelatin, 0 to 1 percent by weight monoglyceride, and 0 to 11 percent by weight lactose, with the proviso that the weight ratio of caseinate to gelatin be greater than 1:1 and
   B. spray drying the emulsion in the presence of from 0.5 percent by weight to 2.0 percent by weight silicon dioxide having a particle size of 1 millimicron to 1 micron, to form a non-agglomerated powder.

* * * * *